United States Patent [19]

Henry et al.

[11] Patent Number: 4,741,899
[45] Date of Patent: May 3, 1988

[54] PROCESS FOR ARRESTING THE PROLIFERATION OF ORGANISMS THAT CONVERT AXILLARY SECRETIONS TO MALODOROUS MATERIALS

[75] Inventors: Sydney M. Henry, Westfield; Gene Jacobs, Montclair; Val F. Cotty, Westfield, all of N.J.

[73] Assignee: Bristol-Myers Company, New York, N.Y.

[21] Appl. No.: 501,306

[22] Filed: Jun. 6, 1983

[51] Int. Cl.⁴ .......................... A61K 7/32; A61K 9/07; A61K 9/12

[52] U.S. Cl. .................................. 424/47; 424/DIG. 5; 424/65; 514/937; 514/938; 514/969

[58] Field of Search ............................................. 424/65

[56] References Cited

U.S. PATENT DOCUMENTS

| | | | |
|---|---|---|---|
| 2,868,802 | 1/1959 | Hueni | 424/168 X |
| 3,312,709 | 4/1967 | MacMillan | 424/65 |
| 3,326,768 | 6/1967 | MacMillan | 424/65 |
| 3,527,864 | 9/1970 | MacMillan et al. | 424/65 X |
| 3,624,200 | 11/1971 | Moffett | 424/65 |
| 3,767,786 | 10/1973 | MacMillan | 424/65 |
| 3,775,538 | 11/1973 | DeSalva et al. | 424/65 |
| 3,953,599 | 4/1976 | MacMillan | 424/65 X |
| 4,010,252 | 3/1977 | Hewitt | 424/47 |
| 4,226,850 | 10/1980 | Packman et al. | 424/47 |
| 4,234,566 | 11/1980 | Packman et al. | 424/47 |

OTHER PUBLICATIONS

Saha, Indian Journal, Medical Research, 11/11/76, pp. 1677 to 1679.

Primary Examiner—Dale R. Ore
Attorney, Agent, or Firm—Charles J. Zeller

[57] ABSTRACT

A process for arresting the proliferation of microorganisms which convert axillary secretions into malodorous materials by treating these axillary secretions with a composition containing a compound selected from the group consisting of tripelennamine, phenindamine, hexylcaine, tetracaine, naphazoline, xylometazoline, pyrilamine and pharmaceutically acceptable salts thereof.

12 Claims, No Drawings

PROCESS FOR ARRESTING THE PROLIFERATION OF ORGANISMS THAT CONVERT AXILLARY SECRETIONS TO MALODOROUS MATERIALS

This invention relates to a process for arresting the proliferation of aerobic diphtheroids, staphylococci and micrococci which convert axillary secretions in a subject to malodorous materials. More particularly, it concerns a process of the aforesaid type in which the axillary secretions are apocrine gland secretions.

The art has long appreciated that axillary sweating is caused by two types of sweat glands; the eccrine sweat glands and the apocrine sweat glands. Products that are designed to inhibit perspiration are targeted to act on the eccrine sweat glands. The development of axillary odor, however, is thought to be primarily due to the action of the species of aerobic diphtheroids, staphylococci and micrococci on apocrine gland secretions.

It has now been found that the proliferation of representative species of aerobic diphtheroids, staphylococci and micrococci and the development of malodorous products due to the action of these organisms on apocrine sweat can be arrested by treating the secretion of the axilla of a subject with a material selected from the group consisting of tripelennamine, phenindamine, hexylcaine, tetracaine, naphazoline, xylometazoline, pyrilamine and pharmaceutically acceptable salts thereof (hereinafter referred to as the active material).

It has been suggested in the prior art to use certain antihistamines alone or in combination with astringent metallic salts for retarding or inhibiting perspiration. In this connection, see the U.S. Pat. Nos. 4,226,850 and 4,234,566 to Packman. In column 3 beginning at line 56 of each of these patents, the patentee discloses that the compositions of his invention use antihistamines to inhibit the secretion or excretion of substances which give rise to offensive odors.

It is clear from these teachings that Packman was concerned with inhibition of glandular secretions and not arresting the growth of organisms in axillary secretions and particularly, secretions from the apocrine glands as is characteristic of the present invention. Further, the test procedure used by the patentee is traditionally used only for measuring the inhibition of eccrine sweating as opposed to deodorancy. The above patents are devoid of any experimentation to demonstrate an effect of antihistamines on apocrine glands or secretions therefrom.

It has also been suggested in the prior art that certain antihistamines exhibit antimicrobial activity. Of interest in this regard are two literature references. One is an article by P. K. Saha et al entitled "Antimicrobial Activity of Antihistaminic Drugs" in the Indian J. Med. Res. 64, 11, November 1976, p. 1677-1679. The other is an article by the same authors in J. Appl. Bacteriol. 41, (2) 1976, p. 209-214. These papers are concerned with in vitro studies of the effect of certain antihistamines in a culture medium or in vivo studies in mice for treatment of certain infections. They are not concerned with arresting axillary odor development as is the case with the present invention. Furthermore, as is clear from these articles, there was great variation among the antihistamines tested regarding their antibacterial activity. Lastly, it is to be noted that the only materials used in this invention that can be characterized as antihistamines are tripelennamine, phenindamine, and pyrilamine and this was not disclosed in these literature references.

In the J. Clin. Pharm. Vol. 10, 1970, p. 235-246, Goodall describes a study in which certain adrenergic and cholinergic blocking agents were tested as sweat inhibiting agents. Among the compounds tested by Goodall for this purpose were tripelennamine HCl and phenindamine tartrate. However, there is no teaching in this reference that these materials are useful for inhibiting apocrine sweating or for arresting the proliferation of aerobic diphtheroids, staphylococci and micrococci in axillary secretion to prevent the formation of malodorous materials.

In practicing the process of this invention, the active material is applied to the axilla of the subject in which the axillary secretions and particularly apocrine sweat is present for sufficient time to arrest the proliferation of the axillary organism. The active material will generally be distributed in a vehicle that can bring it into contact with the axillary secretions. The quantity of active material that will be contained in the vehicle may vary somewhat. All that is required is that it be present in sufficient concentration in the vehicle so as to arrest the proliferation of said organism in the axillary secretions. Generally, said active material will be present in said vehicle in the range of from about 0.1% to about 10% by weight based on the total weight of the composition. In a preferred aspect of this invention, this concentration will be from about 1% to about 5% on the same weight basis.

Various vehicles may be used in accordance with the present invention. All that is required is that the active ingredient be soluble in or solubilized or suspended in the vehicle. Thus, the vehicle may be a simple solvent system, a cream, lotion, ointment, cosmetic stick, aerosol system, etc.

The following are typical examples of a variety of vehicles in which active materials employed in the present invention may be distributed. Any of the active materials mentioned above may be incorporated in these vehicles. The percentages indicated in the Examples below and elsewhere in this specification, unless otherwise specified, are percentages by weight based on the total weight of the composition.

|  | % by Wt. |
|---|---|
| Deodorant Aerosol | |
| Deodorant active | 5.0 |
| Propylene glycol | 3.0 |
| SD-40 Anhydrous alcohol | 47.0 |
| Fragrance | 2.5 |
| Isobutane QS to | 100.0 |
| Roll-On Lotion Deodorant | |
| Carboxyvinyl polymer, 941 | 0.1500 |
| Triethanolamine, 98% | 0.0855 |
| Disodium edetate, dihydrate | 0.1000 |
| Cetyl alcohol | 0.5000 |
| Glyceryl monostearate, non-self emulsifying | 2.5000 |
| Deodorant active | 5.0000 |
| Isopropyl palmitate | 2.0000 |
| Mineral oil, 55-65 SUS | 1.0000 |
| Sodium lauroyl isethionate | 0.5000 |
| Glycerin, anhydrous | 4.8120 |
| Monomethylol dimethyl hydantoin | 0.2500 |
| Perfume | 0.3000 |
| Water, deionized QS to | 100.0000 |
| Deodorant Stick | |
| Propylene glycol | 61.00 |
| Sorbitol solution, 70% | 5.00 |

-continued

| | % by Wt. |
|---|---|
| Sodium stearate C-7 (Witco) | 7.00 |
| Color FD&C Yellow #6 (1.0% solution) | 0.12 |
| Deodorant active | 5.00 |
| Perfume | 1.50 |
| Water, deionized    QS to | 100.00 |
| Deodorant Cream | |
| Colloidal magnesium aluminum silicate, HV | 1.4000 |
| Sodium phosphate, dibasic, anhydrous | 0.3500 |
| Sodium hydroxide, pellets | 0.0800 |
| Carboxyvinyl polymer, 934 | 0.2000 |
| Sorbitol solution, 70% | 2.3000 |
| Glycerin, anhydrous | 2.8870 |
| Isopropyl palmitate | 3.6000 |
| Partial sodium salt of N—lauryl-B—Iminopropionate | 1.6000 |
| Lanolin, anhydrous | 1.0000 |
| Glyceryl monostearate, non-self emulsifying | 2.7000 |
| Cetyl alcohol | 1.2000 |
| Deodorant active | 5.0000 |
| Stearic acid, T.P., flakes | 13.0000 |
| Monomethylol dimethyl hydantoin | 0.2500 |
| Perfume | 0.5000 |
| Water, deionized    QS to | 100.0000 |
| Deodorant Stick | |
| Deodorant active | 5.00 |
| Stearyl alcohol | 10.00 |
| Castorwax MP 80 | 4.00 |
| FT 300 Wax | 2.00 |
| Fluid AP | 3.00 |
| Ionol CP | 0.05 |
| Silicone 7158 | 44.95 |
| Talc 5251 | 25.00 |
| SD-50 Anhydrous alcohol | 5.00 |
| Brij 35 | 1.00 |
| | 100.00 |
| Deodorant Stick | |
| Deodorant active | 5.00 |
| Stearyl alcohol | 8.50 |
| Castorwax MP 80 | 5.00 |
| FT 300 Wax | 2.00 |
| Fluid AP | 3.00 |
| Ionol CP | 0.05 |
| Silicone 7158 | 51.45 |
| Talc 5251 | 25.00 |
| | 100.00 |

The following Examples are given to further illustrate the present invention. It is understood, however, that the invention is not limited thereto.

EXAMPLE 1

(BO 1540-553)

| Ingredients | % by Wt. |
|---|---|
| Phenindamine tartrate | 5 |
| Sodium sulfate | 20 |
| Deionized water    QS to | 100 |

EXAMPLE 2

(BO 1540-588)

| Ingredients | % by Wt. |
|---|---|
| Tripelennamine HCl | 5 |
| Sodium sulfate | 5 |
| Deionized water    QS to | 100 |

EXAMPLE 3

(BO 1540-768)

| Ingredients | % by Wt. |
|---|---|
| Phenindamine tartrate | 5 |
| Deionized water | 95 |

To test the activity of the compounds employed in the present invention in arresting the proliferation of axillary organisms (e.g. corynebacteria and staphylococci) the following in vitro study was carried out:

Test Procedure

Aqueous solutions (or suspensions) were prepared for each test substance. Serial two-fold dilutions of the above were then made in liquid culture medium. Each tube (10 ml of liquid) in the dilution series was inoculated with 0.2 ml of a 1:500 dilution of 24 hr. culture of bacteria. After 24 hrs. at 35° C., tubes showing turbidity (growth) were noted. All non-turbid dilutions were subcultured to liquid growth medium and incubated an additional 24 hrs. at 35° C. The lowest concentration of substance which yielded no growth upon subculture was noted as the minimum inhibitory (bactericidal) concentration (=MIC).

The results of this study are summarized in Table I below. The numbers appearing in columns 2 and 3 give the minimum inhibitory concentration in percent (MIC %) for the materials tested i.e. the minimum concentration in percent of the agent tested which will inhibit the proliferation of the test organisms. The entries in the last column are judgments with respect to the activity of the agent tested.

TABLE I

In vitro Studies - Summary

| | MIC (%) - cidal | | |
|---|---|---|---|
| | Staph (Axilla) | Diphth (Axilla) | Comments |
| Phenindamine tartrate | 0.04 | 0.08 | Good Activity |
| Tripelennamine HCl | 0.63 | 0.31 | " |
| Naphazoline HCl | 0.31 | 0.31 | " |
| Xylometazoline HCl | 0.08 | 0.04 | " |
| Hexylcaine HCl | 0.16 | 0.16 | " |
| Tetracaine HCl | 0.08 | 0.08 | " |
| Pyrilamine maleate | 0.63 | 0.63 | " |

Three in vivo studies were also carried out to further confirm the ability of the compounds employed in this invention to arrest the proliferation of axillary organisms in axillary secretions. In these studies, the criteria for effectiveness was taken as the ability of the agent to inhibit or neutralize axillary odor. The procedure and materials tested were as follows:

STUDY I

Subjects

12 Adult Males

Materials

5% tripelennamine HCl in aqueous 5% sodium sulfate, BO 1540-588

Method

Following a control (or 24 hour) evaluation, both axillae were washed with Ivory soap and water. The test product was applied according to a randomly pre-assigned axilla allocation. Four panelists had product applied to the left axilla and eight to the right. The other axilla of each subject was left untreated to serve as a control. Odor evaluations were made 3, 6 and 24 hours later. The same procedure was repeated the second day.

Three judges were used for the study. An odor scale of 0–10 was employed for these observations with 0 indicating the absence of detectable odor and 10 very strong odor.

STUDY II

Subjects 16 adults (1 female, 15 males)

Materials

5% phenindamine tartrate in aqueous 20% sodium sulfate (BO 1540-553)

Method

Following a control evaluation, both axillae were washed with Ivory soap and water. The test product was applied according to a randomly pre-assigned axilla allocation. The other axilla of each subject was left untreated to serve as a control. Odor evaluations were made at 3, 6, and 24 hours later. The same procedure was repeated the second day.

Three judges were used for the study. An odor scale of 0–10 was employed for these observations with 0 indicating the absence of detectable odor and 10 very strong odor.

STUDY III

Subjects 11 adult males

Materials

5% phenindamine tartrate in aqueous 20% sodium sulfate (BO 1540-769)

5% phenindamine tartrate in water (BO 1540-768)

Method

Following a control evaluation, both axillae were washed with Ivory soap and water. The test products were applied according to a randomly pre-assigned axilla allocation. Odor evaluations were made at 3, 6, and 24 hours after the second product application.

Three judges were used for the study. An odor scale of 0–10 was employed for these observations with 0 indicating the absence of detectable odor and 10 very strong odor.

The results of these studies are summarized in Table II below.

TABLE II

| Product | Deodorant Panel Results | | Results |
|---|---|---|---|
| | Actives | Excipients | |
| Phenindamine Sol. BO 1540-553 (EXAMPLE 1) | 5% Phenindamine tartrate | 20% sodium sulfate in water | Significant odor reduction vs. untreated |
| Tripelennamine Sol. BO 1540-588 (EXAMPLE 2) | 5% Tripelennamine HCl | 5% sodium sulfate in water | Significant odor reduction vs. untreated |
| Phenindamine Sol. BO 1540-768 (EXAMPLE 3) | 5% Phenindamine tartrate | water | Significant odor reduction not different from Example 1 |

Although the invention has been described with reference to specific forms thereof, it will be understood that many changes and modifications may be made without departing from the spirit of this invention.

What is claimed is:

1. A process for arresting the proliferation of aerobic diptheroids, staphylococci and micrococci which convert axillary secretions into malodorous materials, which comprises treating said axillary secretions in the axilla of a subject with a composition comprising a compound selected from the group consisting of hexylcaine, tetracaine, naphazoline, xylometazoline and pharmaceutically acceptable salts thereof.

2. A process according to claim 1 in which said composition comprises an aqueous composition containing said compound.

3. A process according to claim 1 in which said composition comprises a cream containing said compound.

4. A process according to claim 1 in which said composition comprises a lotion containing said compound.

5. A process according to claim 1 in which said composition comprises an ointment containing said compound.

6. A process according to claim 1 in which said composition comprises a cosmetic stick containing said compound.

7. A process according to claim 1 in which said composition comprises an aerosol composition containing said compound.

8. A process according to claim 1 in which said compound is present in said composition that the concentration is in the range of from about 0.1% to about 10% by weight based on the total weight of said composition.

9. A process according to any one of claims 1–8 in which said compound is naphazoline hydrochloride.

10. A process according to any one of claims 1–8 in which said compound is xylometazoline hydrochloride.

11. A process according to any one of claims 1–8 in which said compound is hexylcaine hydrochloride.

12. A process according to any one of claims 1–8 in which said compound is tetracaine hydrochloride.

* * * * *